United States Patent [19]

Miller, Jr.

[11] Patent Number: 5,734,093
[45] Date of Patent: Mar. 31, 1998

[54] METHOD AND APPARATUS FOR DETERMINING PHYSICAL PROPERTIES OF A GAS FOR USE IN RHEOMETRY

[75] Inventor: Theodore E. Miller, Jr., Midland, Mich.

[73] Assignee: The Dow Chemical Company, Midland, Mich.

[21] Appl. No.: 768,744

[22] Filed: Dec. 17, 1996

Related U.S. Application Data

[60] Provisional application No. 60/008,855 Dec. 19, 1995.
[51] Int. Cl.$^6$ .................................................. G01N 9/00
[52] U.S. Cl. .................................... 73/30.03; 73/149
[58] Field of Search ............................... 73/149, 54.04, 73/30.03

[56] References Cited

U.S. PATENT DOCUMENTS

| | | | |
|---|---|---|---|
| 3,520,179 | 7/1970 | Reed | 73/554.04 |
| 3,952,577 | 4/1976 | Hayes et al. | 73/55 |
| 3,962,916 | 6/1976 | Bouchy et al. | 73/149 |
| 4,027,526 | 6/1977 | Osmers | 73/54 |
| 4,527,418 | 7/1985 | Arcara | 73/30 |
| 4,677,841 | 7/1987 | Kennedy | 73/30 |
| 4,750,351 | 6/1988 | Ball | 73/55 |
| 4,817,416 | 4/1989 | Blanch et al. | 73/55 |
| 4,934,178 | 6/1990 | Jones | 73/32 R |
| 4,956,793 | 9/1990 | Bonne et al. | 73/30.01 X |
| 4,956,996 | 9/1990 | Morris | 73/149 |
| 4,984,457 | 1/1991 | Morris | 73/149 |
| 4,987,775 | 1/1991 | Chobotov | 73/149 |
| 4,992,487 | 2/1991 | Rao | 523/303 |
| 5,014,545 | 5/1991 | Rao | 73/55 |
| 5,074,146 | 12/1991 | Orr et al. | 73/149 |
| 5,147,612 | 9/1992 | Raal | 422/99 |
| 5,172,585 | 12/1992 | Gleissle | 73/54.04 |
| 5,257,529 | 11/1993 | Taniguchi et al. | 73/54.09 |
| 5,307,668 | 5/1994 | Vander Heyden | 73/30.02 |
| 5,347,852 | 9/1994 | Mode | 73/54.04 |
| 5,383,352 | 1/1995 | Krawetz et al. | 73/54.01 |
| 5,551,282 | 9/1996 | Vander Heyen | 73/30.03 |

FOREIGN PATENT DOCUMENTS

| | | | |
|---|---|---|---|
| 0591639A2 | 4/1994 | European Pat. Off. | |
| 59-20814A | 2/1984 | Japan. | |
| 232536 | 10/1969 | Russian Federation. | |
| 714-156 | 2/1980 | U.S.S.R. | 73/149 |
| 2226142 | 6/1990 | United Kingdom. | |

OTHER PUBLICATIONS

McGraw–Hill Encyclopedia of Science and Technology, 1977, V5, pp. 363–364.
F. Kohlrausch: "Prakitsche Physik". Band 1. Ed: B.G. Teubner, Stuttgart (1985), vol. 1, pp. 377–381.
René Suardet: "Thermodynamique" Ed: J.B. Baillière et Fils, Paris (1969), pp. 74–81.

*Primary Examiner*—Hezron E. Williams
*Assistant Examiner*—Jay L. Politzer

[57] ABSTRACT

A method and apparatus for determining a physical property of a gas in a confined space. Gas of known volume, pressure and temperature is placed in communication with a confined space containing gas at known pressure to determine the volume of gas in the confined space using computations based on the gas laws. Alternatively, gas of known pressure, volume, and temperature may be placed in communication with a confined space containing gas at known volume to determine the pressure of gas in the confined space prior to communication with the gas of known properties. Gas volume determinations are useful, for example, to perform rheological characterizations of liquid samples.

20 Claims, 1 Drawing Sheet

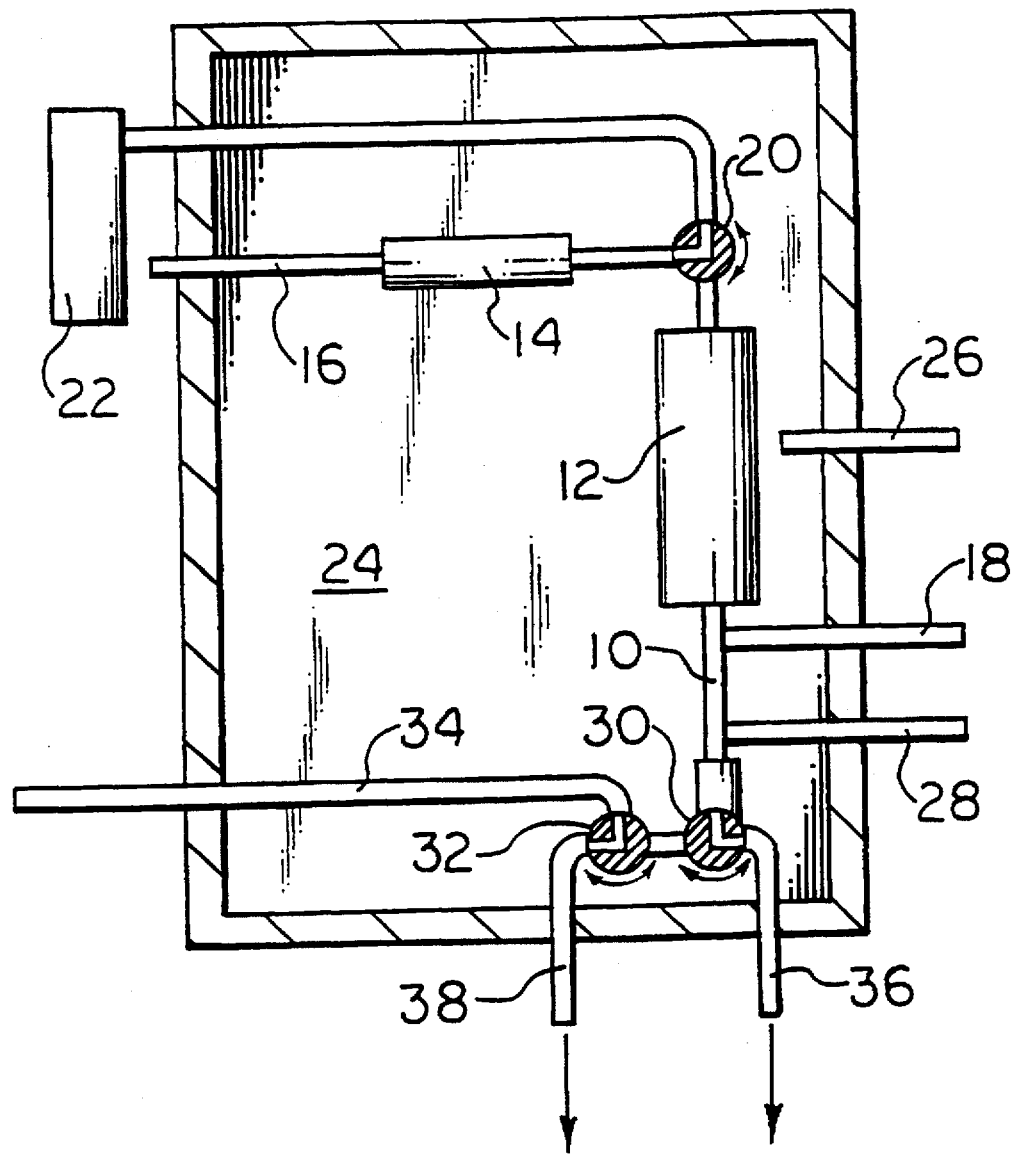

METHOD AND APPARATUS FOR DETERMINING PHYSICAL PROPERTIES OF A GAS FOR USE IN RHEOMETRY

CROSS-REFERENCE TO RELATED APPLICATION

This application claims the benefit of U.S. Provisional Application No. 60/008,855, filed Dec. 19, 1995.

BACKGROUND OF THE INVENTION

The present invention relates to the field of determining physical properties of a gas, particularly as these properties relate to the field of rheometry.

Information on the flow characteristics of fluids is important for efficient plant operation in some industries. Non-Newtonian liquids show non-linear flow responses when force or stress is applied; in other words, their viscosities are dependent on the rate of shear. Thus, traditional viscosity measurements, operating at single shear rates, are insufficient to determine full rheological behavior of non-Newtonian liquids. U.S. Pat. No. 5,257,529 to Taniguchi et al. shows that full rheological measurements can be obtained for non-Newtonian fluids using calculations based on the gas laws as a liquid flows into a sealed vessel to determine the flow rate of a liquid. This type of calculation requires accurate knowledge of the amount of gas in the sealed vessel.

The art of rheological measurement would be improved by a more efficient method and apparatus for determining the volume of gas in a vessel, particularly under conditions in which gas volume is changing.

SUMMARY OF THE INVENTION

The present invention permits determination of the physical properties of a gas in a confined space. This invention has many applications, for example, determining the volume of air space remaining in a storage tank in order to determine the quantity of product in the tank. Another application is gas pressure determination in a volume that is inaccessible to conventional measuring devices. This may be due to physical shape or other conditions such as radiation that would render in situ devices inoperable.

A preferred application is in determining rheological properties of a sample where the flow rate of the sample is determined based on the gas laws as the sample flows into an analysis chamber. Knowledge of the initial pressure and volume of gas in the analysis chamber are critical to the accuracy of the gas law calculations. Thus, if a viscous sample clings to the chamber walls rather than completely emptying from the analysis chamber, the resulting change in the gas volume of the analysis chamber could lead to inaccurate rheometry measurements for subsequent samples analyzed with the same apparatus. The present invention permits updating knowledge of the gas volume in the analysis chamber before sample analysis and thus permits accurate on-line rheometry analysis of even high viscosity samples.

One embodiment of the present invention is a method of determining a physical property of a gas in a first confined space comprising the following steps. A first volume of gas is provided within the first confined space. A second volume of gas is provided within a second confined space. The pressure and the volume of the gas in the second confined space is determined. The first confined space is placed in communication with the second confined space to form a conjoined space. The pressure of the gas in the conjoined space is determined. A physical property associated with the gas in the first confined space is determined based on the above pressure and volume determinations.

If the physical property to be determined is the volume of gas in the first confined space, then the method preferably further comprises the step of determining the pressure of the gas in the first confined space before placing the first confined space in communication with the second confined space. To determine the volume of gas in the first confined space, information on the pressure of the gas in the first confined space is used in combination with the gas pressure determinations for the second and conjoined spaces.

Another embodiment of the present invention is an apparatus suitable for determining a physical property of a gas in a first confined space. The apparatus generally comprises the first confined space; a second confined space being isolatable from and capable of communication with the first confined space; and means for determining gas pressure in the second confined space. If the physical property to be determined is gas volume, then the apparatus preferably further comprises means for determining gas pressure in the first confined space.

BRIEF DESCRIPTION OF THE DRAWING

The FIGURE is a schematic diagram of an embodiment of the apparatus of the present invention.

DETAILED DESCRIPTION OF THE INVENTION

One embodiment of the invention is a method which generally comprises introducing an injection of high pressure gas of known volume, pressure and, preferably, known temperature into a confined space containing a gas for which a physical property is to be determined; this confined space will be referred to herein as a "first confined space." The term "second confined space" as used herein refers to a confined space, preferably containing a known volume of gas, from which pressurized gas can be placed in communication with or injected into the first confined space. The term "conjoined space" refers to the first and second confined spaces taken together when the two confined spaces are in communication and gas combines freely between them. Thus, when the spaces are described herein as the "first confined space" or the "second confined space," reference is being made to a time when the spaces are not in gas communication with each other.

The confined spaces should be substantially air tight vessels such that any loss of gas from the confined spaces is negligible when obtaining pressure measurements so accurate pressure measurements may be obtained. Preferably, each confined space is of fixed volume such that the volume of the confined space itself does not change significantly even though the amounts of sample and gas within a confined space may change. The walls of the confined spaces should be of sufficient strength to withstand the pressures exerted without changing the confined space volume, within the accuracy requirements of the measurement.

As used herein, the term "determining" includes directly measuring, calculating, or knowing a property. A property may be known as a constant. For example, the volume of gas in the second confined space may be known if the volume of gas is the same as the internal volume of the second confined space in which it is contained and the second confined space is not contaminated with non-gas species. Preferably, a dry gas is selected for use in the second confined space so that liquid will not condense in the space upon a change in pressure or temperature. In addition, the gas in the second confined space is preferably at a higher pressure than the gas in the first confined space to minimize the likelihood of non-gas material from the first confined space entering the second confined space when the spaces are placed in communication with each other.

Pressure measurements and computations based on the gas laws may be used to determine the gas volume in the first confined space. For example, the volume of gas in the first confined space may be determined based on the following, or equivalent, equation:

$$V_1 = V_2 (P_2 - P_3)/(P_3 - P_1) \quad \text{Equation (1)}$$

wherein $V_1$ = the volume of the gas in the first confined space;

$V_2$ = the known volume of the gas in the second confined space;

$P_1$ = the gas pressure in the first confined space when isolated from the second confined space;

$P_2$ = the gas pressure in the second confined space when isolated from the first confined space; and $P_3$ = the gas pressure in the conjoined space.

Using the principles of the present invention, this equation may be derived from the well-known gas law equation $P_i V_i = n_i R T_i$ which describes the relationship of the physical properties of pressure, volume, moles of gas, and absolute temperature (degrees Kelvin) in a single contained space. Of course, other equations may be derived based on the gas laws and used equally well. In the present invention, the volume of gas in the conjoined space (subscript 3) equals the sum of the volumes of gas in the first and second confined spaces. Thus, $P_3 V_3 = n_3 R T_3$ becomes $P_3 (V_2 + V_1) = (n_1 + n_2) R T_3$. Substituting $n_1 = V_1 P_1 / R T_1$ and $n_2 = V_2 P_2 / R T_2$ into the equation immediately above and rearranging gives:

$$V_1 = (P_2 V_2 T_3 / T_2 - P_3 V_2)/(P_3 - (P_1 T_3 / T_1)) \quad \text{Equation (2)}$$

which simplifies to Equation (1) when the temperatures in the first confined space ($T_1$), the second confined space ($T_2$) and the conjoined space ($T_3$) are assumed to be the same, i.e. $T_1 = T_2 = T_3$. Therefore, the gas in the first confined space is preferably at essentially the same temperature as the gas in the second confined space such that any difference in temperature would not affect the pressure and volume determinations within the accuracy requirements. Temperature control of the first and second confined spaces may be maintained, for example, by heated air, steam, electrical tracing with temperature control, or with a water bath surrounding the confined spaces in combination with insulation. Temperature control also minimizes effects due to cooling and heating associated with expansion and contraction of gas.

Alternatively, temperature variations may be considered by determining the temperatures of the gas within the first and second confined spaces, and determining the temperature of the gas in the conjoined space. These temperature determinations should correspond to the temperature of the gas in each space at the time the volume and pressure determinations are made. Using the temperature data, the volume of gas in the first confined space may then be determined based on Equation (2) above.

The physical property to be determined by the method of the invention may also be the pressure of gas in the first confined space. As discussed in the summary of the invention describing the method of determining a physical property of a gas in a first confined space, if the physical property to be determined is the volume of gas in the first confined space, then the pressure of gas in the first confined space should be known. Similarly, if the physical property to be determined is the pressure of the gas in the first confined space, then the volume of gas in the first confined space should be known. Using the known information in addition to information on the pressure and volume of the gas in the second confined space and the pressure of the gas in the conjoined space, information on the physical property of interest may be determined. Equations (1) and (2) can be rearranged to solve for the gas pressure in the first confined space ($P_1$). For example, Equation (1) becomes:

$$P_1 = P_3 - (V_2(P_2 - P_3)/V_1).$$

variation of Equation (2) is preferred if temperature variations are to be considered.

A suitable apparatus for determining physical properties of a gas within a first confined space is depicted in the FIGURE which shows first confined space 12 in communication with second confined space 14 via valve means 20. Alternatively, valve means 20 provides communication between second confined space 14 and a source of compressed gas 22; when in this position, gas in the first confined space 12 is isolated from the gas in the second confined space 14. The specific type of valving means used is not critical. Suitable valving means 20 include a ball valve with an L-bore.

The apparatus comprises means for determining gas pressure in the second confined space 14. The apparatus preferably comprises means for determining gas pressure in the first confined space 12 when the physical property to be determined is the volume of gas in the first confined space 12. The gas pressure in confined spaces 12 and 14 may be measured, for example, by pressure transducers 18 and 16 respectively. Preferably, the pressure transducers are also capable of measuring temperature, such as Type TPT 463E-5M available from Dynisco Instruments of Sharon, Mass. The confined spaces 12, and 14 are preferably contained within a temperature controlled region 24 in which the temperature may be measured by thermocouple probe 26.

Preferably, the pressure of gas in the second confined space is greater than the pressure of gas in the first confined space. Thus, the apparatus preferably has means to introduce pressurized gas into the second confined space. For example, a pressurized gas tank 22 may be in communication with second confined space 14 through an appropriately positioned valve 20 (as depicted).

Specifically, with reference to the FIGURE, the volume of gas in first confined space 12 may be determined as follows. First, isolate first confined space 12 from communication with second confined space 14, for example, with valve 20. The second confined space should contain a known or determinable volume of gas. Supply compressed gas from gas tank 22 to second confined space 14 through valve 20. Next, determine the initial pressures of the gas in the first confined space 12 and in the second confined space 14, for example, with pressure transducers 18 and 16 respectively. Then, place the first confined space 12 in communication with the second confined space 14 to form a conjoined space. Communication may be provided by valve 20. Determine the gas pressure in this conjoined space, for example, with pressure transducer 16. Determine the volume of gas in the first confined space based on the pressure determinations for each confined space. The volume determinations may be calculated, for example, based on Equation (1) above.

Volume determination according to this method may be performed on a confined space to be used for rheological measurement on a sample wherein the rheological measurement is determined as sample enters or exits the confined space. Gas volume may be determined before, during (as the confined space fills or empties), or after the rheological analysis; preferably, before. Before sampling, this method is useful to determine the initial gas volume in the first confined space.

To determine rheological properties, the apparatus preferably further comprises a conduit in communication with the first confined space, and a means for determining a difference in pressure across the conduit. In addition, the conduit is preferably in fluid communication with a process line so on-line analysis may be performed.

The word "conduit" as used in this specification denotes any configuration through which fluid may flow to a confined space and which obeys the laws underlying the equations described herein. For example, a suitable conduit may be a tube or a capillary. Preferably, the inner diameter and length of the conduit are known dimensions. The conduit through which sample flows is preferably maintained at the same temperature as the first confined space. Controlled heating permits viscous materials generally to flow more easily. Preferably, the conduit is detachable such that conduits of different length-to-diameter ratio may be substituted.

The rheological properties of a sample may be determined by repeatedly determining the rate at which the sample flows into the first confined space, and using the dimensions of a conduit through which the sample flows into the first confined space to determine the shear strains corresponding to the varying flow rates. To determine shear stresses corresponding to the above shear strains, the changing pressure difference across the conduit is repeatedly determined as the sample enters the first confined space. See, for example, U.S. Pat. No. 5,257,529 to Taniguchi, which is herein incorporated by reference.

More specifically, the rheological properties of a sample may be determined by the following steps. Flow a stream of the sample through a conduit having known dimensions and into the first confined space in which gas volume has been determined as described above. Simultaneously measure differences in pressure across the conduit, and the corresponding rate the sample flows into the first confined space until the flow of sample into the confined space ceases as indicated by the pressure difference across the conduit approaching a minimum value, usually zero. Calculate a set of shear stress data from the differences in pressure across the conduit and calculate the corresponding set of shear strain data from the rates at which sample flows into the first confined space to obtain a stress vs. strain profile.

Four rheological properties can be determined from this test: (1) shear stress, (2) shear rate or shear strain, (3) yield stress, and (4) apparent viscosity.

The first rheological property, shear stress, is given by the equation:

$$shear\ stress = \Delta PD/4L,$$

where

D is the inner diameter of the conduit;
L is the length of the conduit; and
$\Delta P$ is the flow pressure.

If the hydrostatic pressure of a sample opposes flow through the conduit, then $\Delta P = P_1 - P_2 - dgh$, where $P_1$ = pressure at lowermost end of the conduit;
$P_2$ = pressure at uppermost end of the conduit;
dgh = pressure due to the sample in the conduit;
d = density of material;
g = force due to gravity; and
h = height of sample in the conduit.

In general, with viscous samples, the dgh term is negligible so $\Delta P$ simplifies to $P_1 - P_2$, the difference in pressure across the conduit. With less viscous samples where $P_1 - P_2$ is a small term, dgh may be more significant, but if the pressure transducers are zeroed using the sample, the dgh term is then compensated.

The second rheological property, shear strain or shear rate, may be calculated using the equation:

$$shear\ strain = 8Q/DA$$

where

Q is the flow rate of the stream of sample through a conduit;
D is the inner diameter of the conduit; and
A is the cross-sectional area of the conduit.

In the equation above, the flow rate, Q, may be calculated from the rate of change of gas volume in the first confined space, for example, by repeatedly using Boyle's Law as described above to monitor the changing volume over a period of time. Boyle's Law states that, at constant temperature, the volume of a sample of gas is directly proportional to its pressure. Propor-tionality constant k is determined by using the measured initial pressure, and the initial gas volume in the confined space. When dynamic conditions occur, constant k is known and the pressure at time (t) may be monitored; therefore, the volume can be calculated during the dynamic conditions.

Alternatively, or in addition, the volume in the first confined space may be determined during sample testing using the method of the invention. If both volume determinations are done, the accuracy of the volume readings can be checked against each other. If gas is injected into the first confined space during sample flow, then a new Boyle's Law constant should be used to obtain subsequent volume measurements to account for the different gas pressure corresponding to a particular gas volume.

The flow rate may be calculated using the equation:

$$Q = (V_t - V_o)/t,$$

wherein t = the length of time the stream has flowed into the first confined space;
$V_t = P_o V_o / P_t$ = the volume of gas in the first confined space at time, t;
$V_o$ = the initial volume of gas in the first confined space;
$P_o$ = the initial pressure of gas in the first confined space; and
$P_t$ = the pressure of gas in the first confined space at time, t.

The third rheological property, yield value, can be obtained by plotting a graph of shear stress vs. shear rate as those parameters are described above. As is known in the art of rheometry, the yield value is the value at the intersection of the shear stress vs. shear rate curve with the shear stress or Y-axis.

The final rheological property, apparent viscosity, may be obtained by dividing shear stress by shear rate at any point.

The FIGURE shows an example of an apparatus suitable for rheometry analysis of a sample using a confined space in which volume can be determined according to the present invention. The FIGURE shows conduit 10 in communication with first confined space 12. Pressure transducers 18 and 28 together provide means to determine the changing difference in pressure across conduit 10 when sample flows through conduit 10 at varying rates. Conduit 10 is in communication with first confined space 12 and with valve 30. Valve 30 provides communication alternatively between first confined space 12 and valve 32 (the "on" state), or between first confined space 12 and tube 36 (the "off" state). Tube 36 may lead to atmospheric waste or to a by-pass line. Valve 32 provides communication alternatively between sample line 34 and sample return tube 38 (the "off" state) or between sample line 34 and valve 30 (the "on" state). When positioned in the "on" state, valves 30 and 32 provide means for communication between sample inlet line 34 and first confined space 12.

As depicted, the conduit 10 is in fluid communication with first confined space 12 such that hydrostatic pressure of the sample in the confined space will oppose flow of sample through the conduit and into the first confined space. Alternatively, the conduit may be in communication with the first confined space such that the hydrostatic pressure of the sample in the first confined space will not oppose the flow of the sample from the conduit such that the sample freely falls into the first confined space. In this alternative embodiment, a release valve is preferably provided at the bottom of the first confined space to permit emptying of the confined space and to release accumulated pressure.

Specifically, with reference to the FIGURE, the rheological properties of a sample may be determined as follows. The volume of the first confined space is determined using the method of the invention as described. Valves 32 and 30 are adjusted to permit communication between sample line 34 and first confined space 12 ("on" state). Sample flowing through the sample line flows through conduit 10 and into first confined space 12. As sample flows into the confined space, the differences in pressure across conduit 10 are measured by pressure transducers 18 and 28 and this data is stored in a computer, preferably, at least every 0.1 seconds; concurrently, the corresponding pressures of gas in the first confined space are measured frequently by pressure transducer 18 and this pressure data is stored with the above data. The time of occurrence of each pressure measurement is recorded to permit flow rate determinations. Flow rates and the dimensions of conduit 10 are used to determine shear strain values. The temporally corresponding pressure differences across the conduit are used to determine shear stresses. The pressure differences across the conduit and the gas pressures in the confined space are repeatedly and simultaneously measured to obtain a set of data pairs in order to calculate a stress vs. strain profile for the sample as described above.

When flow into first confined space 12 stops because source pressure in line 34 equilibrates with the head space pressure in confined space 12, valve 32 is switched to permit sample to flow again from sample line 34 to bypass line 38. Valve 30 can be adjusted to permit sample to flow out of first confined space 12, through conduit 10 and out tube 36 to waste or to bypass. While sample is exiting first confined space 12, the rheological properties can be measured as they were when the sample entered the confined space by measuring the differences in pressure across the conduit as sample flows through the conduit and simultaneously measuring the flow rates of the sample out of the confined space based on gas law calculations as described herein. The stress vs. strain profile for the sample should be the same whether the sample flows into or out of the first confined space if its shear-rate related viscous behavior is uniform over the entire sample volume.

After the sample has exited the first confined space, repeated bursts of pressurized gas can be injected into the confined space to aid in emptying the confined space by manipulating valve 20 to replenish pressurized gas to the second confined space which can be released into the first confined space. Pressurized gas can also be provided to the first confined space to increase the flow rate of sample out of the first confined space.

After analysis, the method can be used to test for system blockage or measure residual coating of the confined space with sample. The volume calculated should be essentially infinite if the first confined space is opened to the atmosphere, so if a finite volume is determined, then the system is blocked and needs to be cleared using the above procedure. After an analysis, the method can also be used to determine if the remaining gas volume in the first confined space is sufficient for a subsequent test or if the volume should be cleared again.

What is claimed is:

1. A method of determining a physical property of a gas within a first confined space for use in rheometry, the method comprising:

(a) providing a first volume of gas within the first confined space;

(b) providing a second volume of gas within a second confined space;

(c) determining the pressure and the volume of the gas in the second confined space;

(d) placing the first confined space in communication with the second confined space to form a conjoined space;

(e) determining the pressure of the gas in the conjoined space produced by step (d); and (f) utilizing the physical property of the gas within the first confined space in determining a rheological property of a sample, wherein the physical property is determined from steps c) and e), and the rheological property is shear stress, shear strain, yield stress, or apparent viscosity.

2. The method of claim 1 wherein the physical property is the volume of gas in the first confined space and the method further comprises the step of determining the pressure of the gas in the first confined space before step (d).

3. The method of claim 2 wherein the volume of gas in the first confined space is determined based on the following relationship:

$$V_1 = V_2(P_2 - P_3)/(P_3 - P_1),$$

wherein $V_1$ = the volume of the gas in the first confined space;
$V_2$ = the volume of the gas in the second confined space;
$P_1$ = the pressure of the gas in the first confined space;
$P_2$ = the pressure of the gas in the second confined space; and
$P_3$ = the pressure of the gas in the conjoined space.

4. The method of claim 1 wherein the volume of gas in the first confined space is known and the physical property to be determined is the pressure of the gas in the first confined space.

5. The method of claim 1 wherein the first confined space and the second confined space are of fixed volume.

6. The method of claim 1 wherein the gas in the first confined space is at essentially the same temperature as the gas in the second confined space.

7. The method of claim 1 further comprising the steps of:
   (a) before placing the first confined space in communication with the second confined space, determining the temperature of the gas within the first confined space and determining the temperature of the gas within the second confined space; and
   (b) determining the temperature of the gas within the conjoined space.

8. A method of determining the volume of a gas in a first confined space for use in rheometry, the method comprising:
   (a) isolating the first confined space from communication with a second confined space which contains a known volume of gas;
   (b) determining a pressure of the gas in the first confined space;
   (c) determining a pressure of the gas in the second confined space;
   (d) placing the first confined space in communication with the second confined space to form a conjoined space;
   (e) determining a pressure of the gas in the conjoined space;
   (f) determining the volume of the first confined space based on the determinations of steps b, c, and e; and
   (g) utilizing the volume determination from step (f) in determining a rheological property of a sample, wherein the rheological property is shear stress, shear strain, yield stress, or apparent viscosity.

9. An apparatus suitable for determining a physical property of a gas in a first confined space and for determining a rheological property of a sample, the apparatus comprising:
   (a) the first confined space;
   (b) a second confined space being isolatable from and capable of communication with the first confined space;
   (c) means for determining gas pressure in the second confined space;
   (d) a conduit in fluid communication with the first confined space through which the sample is to flow; and
   (e) a means for determining a difference in pressure across the conduit;
wherein the rheological property is shear stress, shear strain, yield stress, or apparent viscosity.

10. The apparatus of claim 9 further comprising means to introduce pressurized gas into the second confined space.

11. The apparatus of claim 9 wherein the physical property is the volume of gas in the first confined space.

12. The apparatus of claim 9 wherein the physical property is the pressure of gas in the first confined space.

13. The apparatus of claim 9 wherein the conduit does not provide fluid communication between the first confined space and the second confined space.

14. The method of claim 1 wherein the sample is a liquid.

15. The method of claim 1 wherein the rheological property is shear strain which is calculated based on the rate at which the sample flows into the first confined space and the dimensions of a conduit through which the sample flows into the first confined space.

16. The method of claim 15 wherein the shear strain is calculated using the relationship:

$$\text{shear strain} = 8Q/DA,$$

wherein

Q is the flow rate of the sample through the conduit;

D is the inner diameter of the conduit; and

A is the cross-sectional area of the conduit.

17. The method of claim 16 wherein the flow rate, Q, is calculated using the equation:

$$Q = (V_f - V_o)/t,$$

wherein t = the length of time the stream has flowed into the first confined space;

$V_f = P_o V_o / P_f$ = the volume of gas in the first confined space at time, t;

$V_o$ = the initial volume of gas in the first confined space;

$P_o$ = the initial pressure of gas in the first confined space; and $P_f$ = the pressure of gas in the first confined space at time, t.

18. The method of claim 1 wherein the rheological property is shear stress which is calculated based on the pressure difference across the conduit as the sample flows into the first confined space.

19. The method of claim 1 further comprising the steps of:
   (h) flowing a stream of the sample through a conduit having known dimensions;
   (i) flowing the stream into the first confined space;
   (j) simultaneously measuring the difference in pressure across the conduit, the corresponding pressure of the gas in the first confined space, and the length of time the stream of sample has been flowing into the first confined space; and
   (k) calculating the shear stress from the difference in pressure across the conduit and calculating the corresponding shear strain from the rate at which the stream of sample flows into the first confined space.

20. The method of claim 19 wherein steps (j) and (k) are repeated.

* * * * *